United States Patent [19]
Riggin et al.

[11] Patent Number: 4,921,787
[45] Date of Patent: May 1, 1990

[54] DETECTION OF ANTIBODIES TO HUMAN IMMUNODEFICIENCY VIRUS BY AGGLUTINATION OF ANTIGEN COATED LATEX

[75] Inventors: Charles H. Riggin, Hopedale; Dante J. Marciani, Hopkinton, both of Mass.

[73] Assignee: Cambridge Bioscience Corporation, Worcester, Mass.

[21] Appl. No.: 44,665

[22] Filed: May 1, 1987

[51] Int. Cl.$^5$ .......................................... G01N 33/569
[52] U.S. Cl. ....................................... 435/5; 436/533; 436/534; 436/811
[58] Field of Search ....................... 436/533, 534, 871; 435/5

[56] References Cited

U.S. PATENT DOCUMENTS

| 4,279,617 | 7/1981 | Masson . | |
|---|---|---|---|
| 4,331,649 | 5/1982 | Chantler et al. . | |
| 4,332,788 | 6/1982 | Mochida et al. | 436/506 |
| 4,397,960 | 9/1983 | Moussebois et al. . | |
| 4,415,700 | 11/1983 | Batz et al. | 436/533 |
| 4,419,453 | 12/1983 | Dorman et al. . | |
| 4,421,896 | 12/1983 | Dorman . | |
| 4,429,040 | 1/1984 | Becker et al. . | |
| 4,542,103 | 9/1985 | Adams . | |
| 4,569,919 | 2/1986 | Toth et al. . | |
| 4,600,698 | 7/1986 | Toth . | |
| 4,629,783 | 12/1986 | Cosand . | |
| 4,725,669 | 2/1988 | Essex et al. | 530/395 |
| 4,735,896 | 4/1988 | Wang . | |

FOREIGN PATENT DOCUMENTS 135352 3/1985 European Pat. Off. .

OTHER PUBLICATIONS

Kitchen et al., "Viral Envelope Protein of HTLV-III is the Major Target Antigen for Antibodies in Hemophiliac Patients", J. Infect. Dis. 153:788–790.

Thorn et al., "Enzyme Immunoassay Using a Novel Recombinant Polypeptide to Detect Human Immunodeficiency Virus env Antibody", J. Clin. Microbiol. 25 (7) 1987 1207–1212.

Barre-Sinoussi et al., Science, 220: 868–871 (1983).

Gallo et al., Science, 224: 500–503 (1984).

Change et al., BIO/Technology, 3: 905–909 (1985).

Cabradilla et al., BIO/Technology, 4: 128–133 (1986).

Van den Hul and Vanderhoff, Br. Polym. J., 2: 121–127 (1970).

Thorn et al., J. Clin. Microbiol., 25(*7(: 1207–1212 (1987).

Burke et al., Diagnosis of Human Immunodeficiency Virus Infection by Immunoassay Using a Molecularly Cloned and Expressed Virus Envelope Polypeptide, Anals of Internal Medicine, 1987, 106:671–676.

Cambridge BioScience, FDA Approval of the Latex Aggltination Assay Using the CBre3 Antigen, News and Information.

Muesing et al., Nucleic Acid Structure and expression of the Human AIDS/Lymphadenopathy Retrovirus, Nature, 1985, 313:450–458.

Primary Examiner—Christine M. Nuckel
Attorney, Agent, or Firm—Saidman, Sterne, Kessler & Goldstein

[57] ABSTRACT

The present invention relates to an assay for determinng the presence of antibodies in a sample to human immunodeficiency virus (HIV) comprising mixing a sample suspected of containing antibodies to HIV with HIV-specific antigen coated, hydroxylated microbeads, evaluating whether agglutination occurs, and determining therefrom the presence of the antibodies to HIV in the sample.

9 Claims, 2 Drawing Sheets

DETECTION OF ANTIBODIES TO HUMAN IMMUNODEFICIENCY VIRUS BY AGGLUTINATION OF ANTIGEN COATED LATEX

FIELD OF THE INVENTION

This invention relates to a latex agglutination assay for the determination of antibodies to human immunodeficiency virus (HIV) with HIV-specific antigen coated, hydroxylated microbeads.

BACKGROUND OF THE INVENTION

Human immunodeficiency virus (HIV) has been shown to be the etiologic agent for acquired immune deficiency syndrome (AIDS) (Barre-Sinoussi et al., "Isolation of a T-lymphotropic retrovirus from a patient at risk for acquired immune deficiency syndrome (AIDS)," *Science*, 220:868-871 (1983) and Gallo et al., "Frequent detection and isolation of cytopathic retroviruses (HTLV-III) from patients with AIDS or at risk for AIDS," *Science*, 224:500-503 (1984)). An antibody response to HIV indicates exposure and infection. Current clinical assays for antibodies to HIV are viral based enzyme immunoassays (EIA). Viral lysate EIAs offer the advantage of high sensitivity but the disadvantage of high rates of false positives, of being slow, requiring several hours to complete a test, and the further disadvantage of requiring sophisticated instrumentation that is not available in all laboratories.

A latex agglutination assay based on purified HIV-specific antigen could offer the advantages of relatively high sensitivity, specificity, speed, and simplicity in situations where the time and technology required for EIA may not be available or appropriate. Latex agglutination is a technology which, unlike EIA, is a direct assay for specific antibodies. This test is based upon cross-linking antigen attached to microbeads with antibodies to form visible aggregates. Latex microbeads are negatively charged and antigen may bind to the microbeads by means of hydrophobic and ionic adsorption rather than by covalent attachment. Because of the fatal nature of HIV infection, it is important that any latex agglutination assay developed for determining the presence of antibodies to HIV in an individual at risk be very accurate.

SUMMARY OF THE INVENTION

The present invention relates to a latex agglutination assay for antibodies to human immunodeficiency virus (HIV) in a sample from a person suspected of being infected. The assay is performed by mixing the sample with HIV-specific antigen coated hydroxylated microbeads, evaluating whether agglutination occurs, and determining therefrom the presence of the antibodies to HIV in the sample.

The invention also relates to kits for employing the latex agglutination assay.

DETAILED DESCRIPTION OF THE INVENTION

Figure 1:
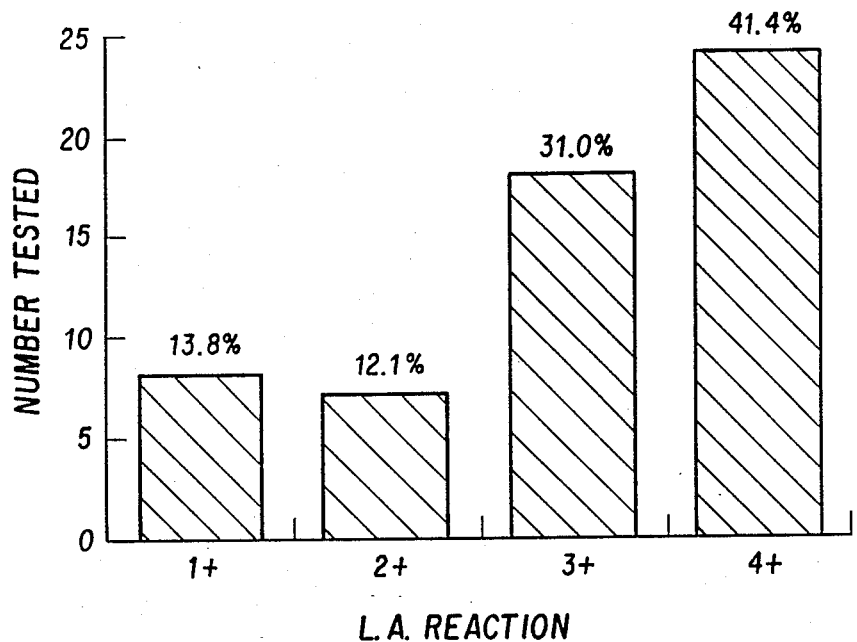
FIG. 1 is a histogram showing the reactivity of positive sera by the latex agglutination test, with the reactivity of positive sera plotted versus the number of samples tested.

This invention relates to a latex agglutination assay for determining the presence of antibodies to HIV. This assay is a direct, rapid, very sensitive, and specific alternative to EIA for antibody testing for HIV. This assay may be used in an emergency clinical setting where there would be a need for a rapid test, minutes or less, for antibodies to the AIDS virus, and in areas lacking EIA instrumentation.

In this invention, the latex hydroxylated microbeads are coated with HIV-specific antigen. The antigens that may be used in this invention includes any immuno-dominant and immuno-specific HIV antigens that have hydrophobic domains able to interact with the latex microbeads. As used herein, HIV antigen refers to polypeptides specific for HIV, such as those derived from the envelope gene of HIV. These HIV antigens may be derived by fractionating HIV, expression of HIV recombinant DNA clones and isolating and purifying selected antigens, or synthetic synthesis of HIV-specific polypeptides.

Preferably, the HIV antigen is obtained through genetic engineering techniques. A suitable recombinant HIV antigen that may be used in this invention is CBre3, derived from the gp120 and gp41 regions of the HIV envelope (env) gene. CBre3 (also identified as Δ G71A) is described in Thorn et al., "An enzyme immunoassay using a novel recombinant polypeptide to detect human immunodeficiency virus," *J. Clin. Microbiol.* (in press 1987) and in U.S. patent application, Ser. No. 825,597, filed Feb. 3, 1986. The recombinant antigen is also on deposit at the American Type Culture Collection (ATCC), accession number 53455.

Other recombinant HIV antigens may be used in this invention, provided that the antigens exhibit extensive hydrophobic domains. Examples of such recombinant HIV antigens are described in Chang, et al., *Bio/Technology*, 3:905-909 (1985); Cabradilla et al., Bio/Technology. 4:128-133 (1985): and U.S. 4,629,783, all incorporated herein by reference.

The latex microbeads used in this invention can be any suitable biologically inert microbeads. As used herein, the term "latex" is understood to mean an emulsion or other dispersion of natural or synthetic rubber particles. Suitable microbeads may include, although are not limited to, polyvinyl toluene, styrene-butadiene latex, styrene-divinyl benzene latex, acrylic latex, and polystyrene latex. The microbeads used in this invention preferably have an average diameter of 0.1 to 3.0$\mu$, more preferably from 0.4 to 1.0 $\mu$.

Hydroxylated microbeads are manufactured by co-polymerization of styrene and hydroxylated styrene monomers in an emulsion of surfactant micelles. Hydroxylated latex is also derived from conventional polystyrene beads by "aging" the beads or by incubation at elevated temperatures (van den Hul and Vanderhoff, "Inferences on the mechanism of emulsion polymerization of styrene from characterization of the polymer end-groups," *Br. Polym. J.*, 2:121-127 (1970)). The sulfate groups present on the surface of polystyrene latex beads are hydrolyzed to hydroxyl groups.

Further, as used in this invention, the latex microbeads have a hydrophobic surface from which hydrophilic hydroxyl groups project. The inventors have discovered that using hydroxylated latex microbeads, in combination with the HIV specific antigen, results in increased activity or the ability of the HIV specific antigen to bind to the antibodies that are being detected. Without being limited in any way, it is believed that this is due to the following phenomena. The hydroxylation of the latex microbeads provides hydrophilic regions on the surface of hydrophobic beads. The HIV antigen is largely hydrophobic and these regions strongly adsorb to the hydrophobic surface of the microbeads. However, HIV antigen also has a few hydrophilic immunodominant regions and these portions interact weakly with the hydrophilic hydroxyl groups. The coating and attachment of the HIV antigen to the hydroxylated microbeads enhances the presentation of the antigen to antibodies and thereby the activity or ability of the antibody to bind to the antigen on one or more beads and subsequently cause measurable amounts of agglutination.

The hydroxylated latex beads may be prepared from HIV antigen coating by adaptation of known means for microbead coating. In the preferred embodiment of this invention, the hydroxylated latex beads are prepared for antigen coating by first suspending the beads in a buffer of pH from about 7 to about 10, preferably a sodium carbonate buffer, pH 9.6. Other buffers are known in the art and may be used in this invention, for example, borate-saline, glycine-saline, and N,N-bis-2-hydroxyethyl glycine. The HIV-antigen, dissolved in a buffer, typically a guanidine-HCl, Tris-HCl buffer, pH from about 7 to 9, is added to the latex bead suspension. Typically a 1 volume antigen to 2 volumes latex suspension will be sufficient to coat the latex beads with HIV-antigen. The latex bead suspension-HIV-antigen mixture is incubated for a time and under conditions sufficient to coat the beads. This is typically accomplished with several hours incubation time at room temperature. Other incubation times and temperatures can, however, be utilized. Next, bovine serum albumin (BSA) in buffered saline is used to block any uncoated portions of the beads. The HIV-antigen coated hydroxylated latex beads are then collected, typically by centrifugation.

The coated latex beads are suspended in a volume of 1% to 10% bovine serum albumin buffer to give a final antigen coated latex bead/buffer concentration of from about 0.4 to about 0.8% weight/volume. The patient samples (or laboratory samples) are also preferably diluted in BSA buffer. Positive control sample with antibody to HIV and negative control sample without virus-specific antibody should then also be diluted in BSA buffer.

The sample containing the antibodies to HIV will typically be a biological sample, although laboratory samples of antibodies may also be assayed. The biological sample may be blood plasma, serum, or whole blood from a patient. The sample may also include other biological fluids and tissue, such as, for example, urine, saliva, tear drops, cerebrospinal fluid, and the like, or a solid or semi-solid such as, for example, tissues, feces, and the like. The sample may be diluted to a range of from 1:0 parts to 1:100 parts sample:buffer (v/v) basis, with a BSA buffer as described above.

The agglutination assay of this invention is performed by mixing the sample suspected of containing antibodies to HIV with the HIV-antigen coated microbead suspension. The ratio of sample to microbead suspension may be any that gives an agglutination reaction for a positive sample. Those skilled in the art will be able to determine this ratio by routine experimentation using standards and controls. In a preferred embodiment of this invention, the ratio is from 5–25 μl microbead suspension and about 5 to 50 μl sample, more preferably 10 to 20 μl microbead suspension and about 15–40 μl sample; and most preferred 15 μl microbead suspension and 25 ul sample. Controls and standards are performed in like manner. The sample and microbead suspension mixture should be mixed for a time sufficient and under conditions to promote any agglutination. Typically, the sample and HIV antigen coated microbead suspension are mixed on a solid plate surface, such as a slide, and mixed by gentle rotation or shaking of the plate. The time required for sufficient agglutination is from about 3 to 5 minutes, typically about 3 minutes. A positive reaction for antibodies to HIV is agglutination visible in bright light. A negative reaction is no agglutination, the sample and microbead suspension mixture being a smooth consistency.

In addition, the materials for use in the assays of the invention are ideally suited for preparation of a kit. Such a kit may comprise a carrier means being compartmentalized to receive in close confinement one or more container means such as vials, slides, and the like. Each of said container means comprises one of the separate elements to be used in the method.

For example, one of said container means may comprise HIV-antigen coated microbeads. A second container may comprise a buffer solution. A third and fourth container with negative and positive controls, respectively are included.

The carrier may also contain, in addition, a plurality of containers each of which comprises different, predetermined and known amounts of antibody to HIV and controls. These latter containers can then be used to prepare a standard curve from which can be interpolated the results obtained from the sample containing the unknown amount of antibody.

The following examples further describe the materials and methods used in carrying out the invention. The examples are not intended to limit the invention in any manner.

EXAMPLE I

Hydroxylated latex beads were prepared for antigen coating by first suspending the beads in sodium carbonate buffer, pH 9.6, collecting them by centrifugation, and then resuspending them in buffer three times more. The final suspension of hydroxylated beads was 5.0% weight/volume in carbonate buffer, pH 9.6; these were sonicated to insure an even distribution. The HIV-antigen dissolved in 6M guanidine-HCl, 50 mM Tris-HCl buffer, pH 8.5, 0.5 mg/ml, was added dropwise to the latex suspension with constant mixing until the guanidine hydrochloride concentration in the reaction was 2.0 M (1 volume antigen to 2 volumes latex suspension). The mixture was incubated for several hours, with mixing, at room temperature. Next, 1% bovine serum albumin in phosphate buffered saline was added until the reaction volume has been increased 5.5 fold. This suspension was incubated for 2 hours, with mixing at room temperature. The latex-antigen beads were collected by centrifugation, the supernatant was removed, and the beads resuspended in 1% bovine serum albumin in phosphate buffered saline, pH 7.6 (BSA buffer). The centrifugation and resuspension were repeated two times. The latex beads were collected by centrifugation, the supernatant removed, and the beads resuspended in a volume of BSA buffer equivalent to 16.67 times the original suspension volume for the adsorption step. This yielded a final latex-antigen concentration of 0.6% weight/volume. The latex-antigen suspension was sonicated to insure an even distribution. The coated latex beads may be stored at 2°-8° C.

EXAMPLE II

The data shown in Table 1 are from 50 individuals tested retrospectively by latex agglutination, Western blot, and EIA with CBre3 coated immunoassay plate. Four samples which were gag only by Western blot (data not shown) were positive by CBre3-latex agglutination even though no gag antigen was present on the latex. There was complete concordance between all samples tested by Western blot, CBre3-latex agglutination, and CBre3-EIA.

TABLE I

Comparison of latex agglutination to Western blot of viral lysates and CBre3-EIA

|  |  | Western blot | | CBre3-EIA** | | Total Tested |
|---|---|---|---|---|---|---|
|  |  | pos* | neg | pos | neg |  |
| Latex Agglutination | pos | 33 | 0 | 33 | 0 | 33 |
|  | neg | 0 | 17 | 0 | 17 | 17 |
|  |  |  |  |  |  | 50 |

*Includes 4 specimens which were gag only and 1 specimen which was p24 negative.
**Optical Density (O.D.) range 0.01 to 0.12 for negative samples and 0.61 to 2.0 for positive samples.

EXAMPLE III

A second set of 29 sera were tested retrospectively comparing latex agglutination, CBre3-EIA, and a commercially available viral lysate based EIA. The results are shown in Table II. There was 100% concordance between all samples tested. Even though the optical densities for some of the specimens by commercial EIA were as low as 0.517, latex agglutination and CBre3-EIA were still able to detect antibodies to HIV in these samples. In this group, samples for latex agglutination were tested both undiluted and diluted 1:10; this dilution did not affect whether a sample scored as positive or negative. However, some of the positives demonstrating high optical densities by EIA had a more intense reaction by agglutination at 1:10 than undiluted. This means that a prozone effect is likely with high titer seropositives.

TABLE II

Comparison of latex agglutination and CBre3-EIA with recombinant env to commercial EIA

|  |  | Commercial EIA* | |
|---|---|---|---|
|  |  | + | − |
| Latex Agglutination | + | 24 | 0 |
|  | − | 0 | 5 |
| CBre-3-EIA** | + | 24 | 0 |
|  | − | 0 | 5 |

*O.D. range for positive samples was 0.517 to >2.0; for negative samples the range was .086 to 0.105 O.D.
**CBre3-EIA O.D. range for positive samples was 0.449 to >2.0; for negative samples the range was 0.102 to 0.162.

In FIG. I are shown the relative intensity of the reactivities of the same 57 positive sera from Tables I and II by latex agglutination. A 4+ reaction is the strongest and most obvious reaction and a 1+ reaction is the least discernible above the lack of reactivity with a negative control. These data indicate that most of the 57 positive sera are strongly reactive by latex agglutination and are therefore easily read.

EXAMPLE IV

An experiment was performed to compare agglutination and CBre3-EIA with respect to end point dilutions of positive sera. Negative serum was used to dilute three different positive sera. Each diluted sample was then assayed by latex agglutination and CBre3-EIA. The results in Table III show similar reactivities by CBre3-EIA and latex agglutination with these three diluted positive sera. This means that latex agglutination with recombinant env has sensitivities similar to EIA with these sera. It should be pointed out that the specimen can be tested undiluted by latex agglutination while EIA generally requires that the specimen be diluted at least 1:20 during the procedure.

TABLE III

Comparison of latex agglutination to CBre3-EIA with diluted sera.

| Serum/Dilution | 1:9 | 1:27 | 1:181 | 1:843 | 1:2400 | |
|---|---|---|---|---|---|---|
| 1 | 4+ | 4+ | 3+ | N | N | Latex Agglutination |
|  | 1.20 | 0.72 | 0.41 | 0.16 | 0.08 | O.D. by CBre3-EIA |
| 2 | 4+ | 4+ | 3+ | N | N | Latex Agglutination |
|  | 1.10 | 0.93 | 0.49 | 0.18 | 0.08 | O.D. by CBre3-EIA |
| 3 | 4+ | 3+ | N | N | N | Latex Agglutination |
|  | 0.70 | 0.47 | 0.16 | 0.08 | 0.02 | O.D.>by CBre3-EIA |

N is no agglutination or a negative reaction; O.D. 0.20 is a negative reaction by CBre3-EIA. Positive sera numbers 1, 2, and 3 were diluted with a negative serum to generate the dilutions indicated.

EXAMPLE V

Figure 2:
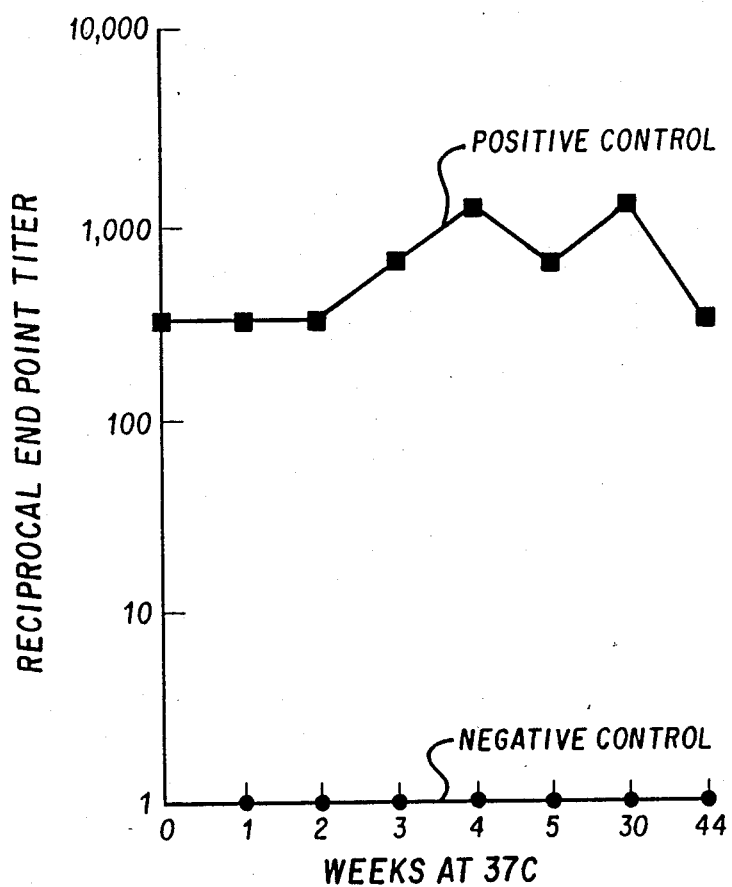
FIG. 2 is a graph showing the thermal stability of a recombinant polypeptide antigen, CBre3, on latex microbeads.

The thermal stability of CBre3 antigen on latex as determined by incubating a preparation at 37° C. and testing aliquots at various times with positive and negative serum. Negative serum was diluted 1:10, positive sera was diluted serially from 1:10 until there was no agglutination. End point titer, the last dilution which had a 1+ agglutination, was plotted versus time at 37° C. The results of this experiment are shown in FIG. 2. In FIG. 2, the closed circles show endpoint titer by agglutination of a serum positive for antibodies to HIV versus weeks at 37° C. for the latex-antigen; open circles show the same for negative serum. These results indicate CBre3-latex has reactivity with positive serum after 44 weeks at 37° C. and no reactivity with negative serum during the same period.

Although the foregoing invention has been described in some detail by way of illustration and example, for purposes of clarity and understanding, it will be obvious that certain changes and modifications may be practiced within the scope of the invention, as limited only by the scope of the appended claims.

What is claimed is:

1. An assay for determining the presence of antibodies in a sample to human immunodeficiency virus comprising contacting a sample suspected of containing antibodies to human immunodeficiency virus (HIV) with hydroxylated microbeads coated with HIV-specific antigen having hydrophobic domains, evaluating whether agglutination occurs, and determining therefrom the presence of antibodies in said sample.

2. The assay of claim 1 wherein said HIV-specific antigen is an antigen from the envelope region of HIV containing hydrophobic domains.

3. The assay of claim 2 wherein said HIV-specific antigen is a recombinant antigen made using genetic engineering techniques.

4. The assay of claim 2 wherein said HIV-specific antigen is obtained by synthetic synthesis of HIV-specific polypeptides.

5. The assay of claim 1 wherein said microbeads has an average diameter of from 0.1 to 3.0 μ.

6. The assay of claim 1 wherein said sample is a biological sample.

7. The assay of claim 6 wherein said biological sample is selected from the group consisting of blood, blood plasma, serum, urine, saliva, tear drops, cerebrospinal fluid, tissue, feces, sperm, and vaginal fluids.

8. The assay of claim 1 wherein said microbeads are suspended in a buffer solution prior to mixing with said sample.

9. An assay for determining the presence of antibodies in a biological sample to human immunodeficiency virus comprising contacting a biological sample suspected of containing antibodies to human immunodeficiency virus (HIV) with CBre3-coated, hydroxylated microbeads, evaluating whether agglutination occurs, and determining there-from the presence of antibodies in said sample.

* * * * *